(12) United States Patent
Suckow et al.

(10) Patent No.: US 8,062,646 B2
(45) Date of Patent: Nov. 22, 2011

(54) TISSUE VACCINES AND USES THEREOF

(75) Inventors: Mark A. Suckow, Granger, IN (US); William R. Wolter, South Bend, IN (US); Morris Pollard, Mishawaka, IN (US)

(73) Assignee: University of Notre Dame, Notre Dame, IN (US)

( * ) Notice: Subject to any disclaimer, the term of this patent is extended or adjusted under 35 U.S.C. 154(b) by 220 days.

(21) Appl. No.: 11/924,459

(22) Filed: Oct. 25, 2007

(65) Prior Publication Data
US 2008/0160049 A1 Jul. 3, 2008

Related U.S. Application Data

(62) Division of application No. 11/209,766, filed on Aug. 24, 2005.

(60) Provisional application No. 60/604,458, filed on Aug. 26, 2004.

(51) Int. Cl.
*A61K 39/00* (2006.01)

(52) U.S. Cl. .................................. 424/277.1

(58) Field of Classification Search .................. None
See application file for complete search history.

(56) References Cited

U.S. PATENT DOCUMENTS

| | | | |
|---|---|---|---|
| 6,227,368 B1 | 5/2001 | Hiserodt et al. | |
| 6,277,368 B1 | 8/2001 | Hiserodt et al. | |
| 6,406,689 B1 | 6/2002 | Falkenberg et al. | |
| 6,699,483 B1 * | 3/2004 | Dalgleish et al. | 424/277.1 |
| 2001/0006631 A1 | 7/2001 | Hiserodt et al. | |

OTHER PUBLICATIONS

Dols, Smith, Meijer, Fox, Hu, Walker, Rosenheim, Moudgil, Doran, Wood, Seligman, Alvord, Schoof, and Urba. Vaccination of women with metastatic breast cancer using a costimulatory gene (CD80)modified, HLA-A2 matched allogeneic, breast cancer cell line: Clinical and Immunological Results. Human Gene Therapy, 2003. vol. 14 pp. 1117-1123.*
Denmeade, Litvinov, Sokoll, Lilja, and Isaacs. Prostate specific antigen (PSA) protein does not affect growth of prostate cancer cells in vitro or prostate cancer xenografts in vivo. Prostate, 2003. vol. 56, pp. 45-53.*
Frost and Sanderson. Tumor immunoprophylaxis in mice using glutaraldehyde-treated syngenic tumor cells. Cancer Research, 1975. vol. 35, pp. 2646-2650.*
Peters, Brandhorst, and Hanna. Preparation of immunotherapeutic autologous tumor cell vaccines from solid tumors. Cancer Research, 1979. vol. 39, pp. 1353-1360.*
Teir and Voutilainen. Effects of intraperitoneally injected suspensions of roentgen irradiated and non-irradiated tumor tissue on the growth of homologous tissue. Acta Pathol. Microbiol. Scand. 1957. vol. 40, pp. 273-282.*

Boring CC, et al. (1993), Cancer statistics. *CA Cancer J Clin*, 43:7-26.
Nomura Amy et al. (2000), *Cancer Epid* Biomark Pre$^y$, 9:883-87.
Brooks JD, et al. (2001), *J Urol* 2001; 166:2034-8.
Hursting SD, et al. (1990), *Prev Med*,19:242-53.
Gann PH. (1999), *JAMA*, 281:1682.
Gann PH, Ma J, Giovannucci E, et al. (*1999*), *Cancer Res.*, 59:1225-30.
Tjoa BA, et al. (*1999*), *Prostate*; 40:125-29.
Tjoa BA, Murphy GP. (2000), *Immunol Lett*, 74:87-93.
Gulley J, et al. (2002), *Prostate*, 53:109-17.
Pollard M, Luckert PH. (1975), *J Natl Cancer Inst*, 54:643-49.
Suckow MA, et al. (1991), *Lab Anim Sci.*, 41:151-56.
Ringler DH, Peter GK, Chrisp CE, et al (1985), *Infect. Immun.*, 49:498-504.
Pollard M, Luckert PH. (1986), *J Natl Cancer Inst.*, 77:583-87.
Pollard M, Luckert PH. (1987), *Prostate*, 11:219-27.
Pollard M. (1998), *Prostate*, 37:1-4.
Hrouda D, et al. (1998), *Br J Urol.*, 82:870-76.
Hrouda D, et al. (2000), *Br J Urol* Int, 86:742-48.
Griffith TS, et al. (2001), *J Natl Cancer Inst*, 93:998-1007.
Charles LG, et al. (2000), *World J Urol*, 18:136-42.
Michael A, et al. (2005), *Clin Cancer Res*, 11:4469-78.
Wang et. al (1993), J. Clin. Invest., 91:684-692.
Shekhar et al. (2001), Cancer Res., 61:1320-1326.
Cunha et al. (2003), *Mt. J. Cancer*, 107:1-10.
Yu-quan Wei (2002), *Anti-Cancer Drugs*, 13:229-235.
Fong et al. (2001), *J. Imm.*, 167: 7150-7156.
Srinivason et al. (2004), *J. Translational Med.*, 2:1-12.
Bergman et al. (2003), *Clin. Canc. Res.*, 9: 1284-1290.
Qui-ming He et al. (2003), *J. Biol. Chem.*, 278 (24): 21831-21886.
Fernandez-Acerno MJ, et al. (2000), *Cancer* 88: 1544-48.
Ohashi Y, et al. (2000), *Anticancer Res.*, 20: 3025-30.
Furbert-Harris et al. (2003), *Prostate*, 57:165-175.
International Search Report, mailed Jul. 22, 2009 in PCT/US 09/35062.

* cited by examiner

*Primary Examiner* — Anne M. Gussow
(74) *Attorney, Agent, or Firm* — Katten Munchin Rosenman, LLP; Denise L. Mayfield

(57) ABSTRACT

Compositions comprising a tissue vaccine that include a mixture of heterogeneous tissue obtained from tumors and connective tissues. Vaccines comprising these compositions are also provided, as well as methods of using the vaccines in the treatment and/or inhibition of tumor growth, and particularly prostate tumor growth and cancers. The preparations may be defined as vaccines comprising tumor cells and connective (stromal) tissues derived from xenogeneic animals. Preparations comprising the tissue vaccines are provided using tissue harvested directly from tumors. Methods for preventing de novo development of cancer are also disclosed. A tissue vaccine comprising glutaraldehyde-(GFT) treated tissue prepared from tumor and connective tissue reduces the incidence of autochthonous prostate cancer. A tissue vaccine comprising a potassium thiocyanate extract (PTE) preparation of a tumor and connective tissue is also provided. The tissue vaccines are demonstrated to reduce the incidence of autochthonous prostate cancer.

12 Claims, 6 Drawing Sheets

LUNG METASTASIS FROM PRIMARY TUMOR

TISSUE VACCINES AND USES THEREOF

CROSS REFERENCE TO RELATED APPLICATIONS

The present application is a Divisional patent application of U.S. Ser. No. 11/209,766, filed Aug. 24, 2005.

BACKGROUND

1. Field of the Invention

The present invention relates generally to the field of vaccines, and more particularly to antitumor and anticancer vaccines. The invention also relates to the field of methods of treating and inhibiting tumor growth, particularly prostate tumor growth and cancer.

2. Related Art

Prostate cancer is a significant cause of cancer mortality in the western world.[1] Because current methods of treatment have shown only limited success in advanced cases, methods to reduce the incidence of disease would yield clear, significant benefit. Previous methods to prevent prostate cancer have focused primarily on dietary factors such as selenium[2,19], dietary fat[4], and lycopene[5,6].

Though some potential benefit of vaccination has been demonstrated for treatment of individuals already having the disease[7,8,9], little work has been done to examine the possibility of preventing prostate cancer through vaccination. U.S. Pat. No. 6,406,689 (Falkenberg et al.)[21] relates to the use of irradiated tumor cells for the prevention and treatment of various cancers, the vaccines therein having been prepared from established cell lines grown in vitro. Hrouda, et al. relates to the immunization of rats with a whole tumor cell vaccine and a non-specific adjuvant.[16,17] A recombinant poxvirus encoding tumor-associated antigens has also been described that was reported to protect rats against transplanted Dunning AT-2 prostate cancer cells.[19] A mixture of cultured allogeneic human prostate cancer cell lines which were inactivated by irradiation were used to extend the median time to disease progression in patients with high PSA values.[20]

These and other described vaccines were derived from single antigens or monoclonal cell cultures, and therefore when administered to an animal, offer limited antigenic challenge, and hence immunity to the animal. Because tumors exist in vivo in an environment composed of multiple cell and tissue types, a need continues to exist in the art for preparations that include a more representative composite of tumor and supportive tissue antigenic species. A need continues to exist in the medical arts for more effective treatments to halt and prevent cancer and tumor growth.

SUMMARY

The present invention is directed to overcoming the above-mentioned and other challenges related to preparations useful in the treatment and prevention of cancer and tumor growth. Embodiments of the present invention are exemplified in a number of implementations and applications, some of which are summarized below.

In one aspect, compositions are provided that comprise a tissue preparation. In some embodiments, the tissue preparation is a tissue vaccine. In some embodiments, the tissue vaccine comprises tumor tissue and connective tissue (stroma).

In some embodiments, the tissue vaccine is described as a heterologous mixture of antigens characteristic of whole tumor tissue and connective (stromal) tissue. In particular embodiments, the tissue vaccine comprises tumor tissue and connective tissue (stroma) that has been processed with a chemical agent. For example, the tumor tissue and connective tissue (stroma) may be processed with glutaraldehyde (GFT), potassium thiocyanate (PTE), or a combination thereof. These embodiments of the tissue preparation may be described as a glutaraldehyde tissue vaccine (GFT) or a potassium thiocyanate extract (PTE) vaccine.

In another aspect, a xenogeneic vaccine is provided. In some embodiments, the xenogeneic vaccine comprises components derived from tumor tissue harvested from one species of animal to prevent or treat tumors in an animal of another species.

In another aspect, methods are provided comprising treating an animal with a tissue vaccine. In some embodiments, the method comprises treating an animal to inhibit tumor growth or to prevent tumor development. The method in some embodiments comprises providing an animal with an effective amount of the tissue vaccine as described herein.

In particular embodiments, a method is provided for specifically treating a tumor, particularly for preventing or inhibiting tumor growth. In some embodiments, the method provides for administering an effective amount of a composition comprising a tissue vaccine to an animal having a tumor. In some embodiments, the tissue vaccine comprises a tumor and connective (stromal) tissue preparation that has been processed and/or treated with potassium thiocyanate or a glutaraldehyde (GFT) vaccine. In some embodiments, this tissue vaccine is described as a potassium thiocyanate extract (PTE) or a glutaraldehyde (GFT) vaccine.

In yet another aspect, a method for inhibiting de novo tumor cell growth is provided. In some embodiments, the method provides for administering an effective amount of a tissue vaccine to an animal. In particular embodiments, the tissue vaccine is a tumor and connective (stromal) tissue preparation that has been processed and/or treated with glutaraldehyde. In some embodiments, this tissue vaccine is described as a GFT tissue vaccine.

In some aspects, methods are provided for treating and/or inhibiting particular types of cancers, such as those characterized as hormone-influenced cancers. By way of example, in some embodiments, the hormone-influenced cancer comprises prostate, breast, testicular, uterine, and/or ovarian cancers.

In yet another aspect, methods are provided comprising immunizing an animal against cancer. In some embodiments, the cancer is a hormone-influenced cancer, such as prostate, breast, testicular, uterine, and/or ovarian cancer or an adenocarcinoma such as prostate, breast and lung cancer. In particular embodiments, the methods comprise immunizing an animal in need thereof with an effective amount of a composition comprising a vaccine comprising a tissue-composite. The tissue vaccine in some embodiments comprises a heterogeneous tissue composition comprising a diverse combination of materials obtained from both tumor and connective (stromal) tissues.

In yet other aspects, methods for preparing a tissue vaccine are provided.

The following abbreviations and acronyms are used throughout the description of the present invention:
CFA—Complete Freund's adjuvant;
GFT Glutaraldehyde-tissue preparation;
LW—Lobund-Wistar;
MEM=minimal essential medium;
MNU=methylnitrosourea;
PSV=prostate/seminal vesicle PTE=Potassium thiocyanate extract;

BRIEF DESCRIPTION OF THE DRAWINGS

The invention will be described in conjunction with the accompanying drawings, in which.

DETAILED DESCRIPTION

Figure 1:
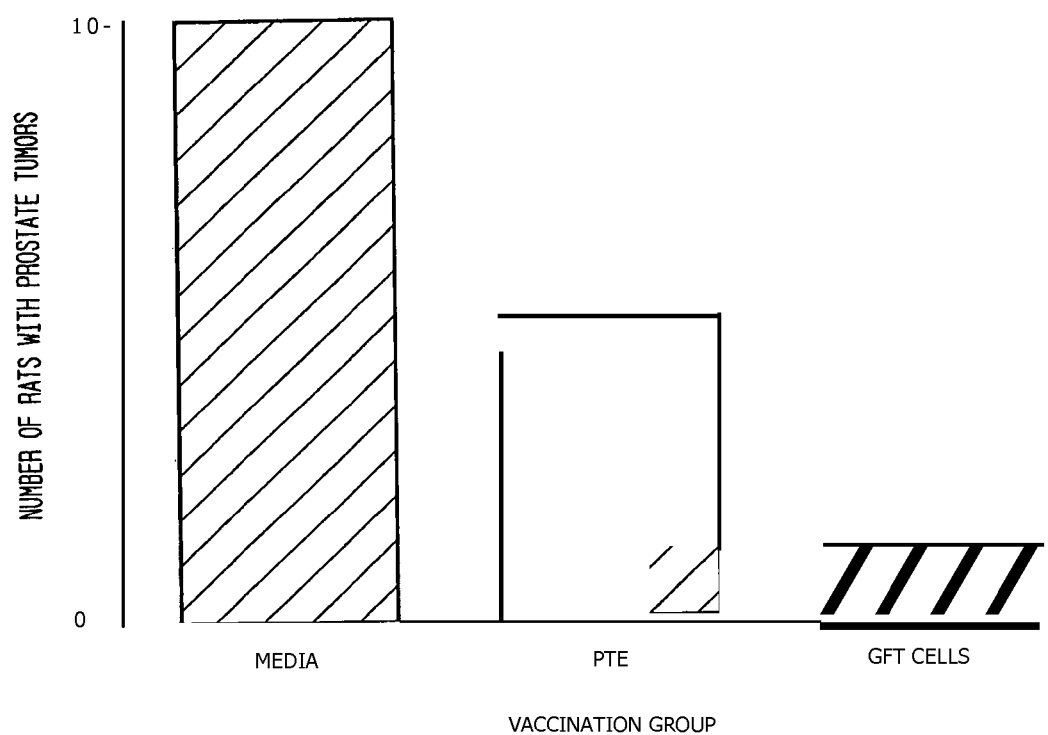
FIG. 1, in accordance with one embodiment of the invention, provides a graph showing the number of rats with de novo prostate tumors following vaccination with media, a potassium thiocyanate extract (PTE) of harvested tumor tissue, or glutaraldehyde-fixed tumor (GFT) cells.

It is advantageous to define several terms before describing the invention It should be appreciated that the following definitions are used throughout this application.

DEFINITIONS

Where the definition of terms departs from the commonly used meaning of the term, applicant intends to utilize the definitions provided below, unless specifically indicated.

The term "stroma" refers to a whole cell mixture comprising animal supportive or connective tissue characteristic of that tissue located in or around a tissue or organ, particularly that connective and/or supportive tissue located in or around a tumor tissue or whole tumor as found in vivo, i.e., in the body. The stromal preparations may not be characterized by a single type or species of cells or proteins. For example, they may be instead characterized by a mixture of diverse antigenic species characteristic of a whole stromal tissue preparation as observed in vivo in association with a whole organ or tumor.

The term "tissue preparation" refers to a heterologous mixture of tumor cell and non-tumor cell tissue. The non-tumor cell tissue may comprise, for example, connective tissue, stroma, blood, serum, bone cells, blood, vessels, or any other animal cell other than tumor cells. The tissue preparation comprises a diverse mixture of defined and undefined antigenic species, and is comprised of antigens present on the surface and inside of whole tumor and associated (connective tissue) non-tumor cells, in a disrupted or intact cell form. A tissue vaccine of the present invention may include whole cells, cell lysates, tissue preparations that include tumor tissue and other tissues, such as connective and supporting tissues (stroma), etc. The term is not intended to be defined as an isolated cellular component or protein, or finite number of strictly enumerated antigenic species characteristic of a tumor cell or a connective tissue alone. Hence, as used herein, the tissue preparation and vaccines prepared there from or method employing them presents numerous targets (antigenic species) that induce an immunogenic response to a multiplicity of tumor tissue and connective tissue antigenic species. A broad spectrum antigenic immune response may thus be elicited in an animal vaccinated with the preparations, and may provide the anti-tumor activity described herein.

The term "tumor" refers to a combination of neoplastic tissue and associated supporting stroma and connective tissue.

The term "vaccine" refers to a preparation that contains components (antigenic species) capable of stimulating an immune response in an animal.

The term "GFT vaccine" refers to a tissue preparation that comprises a combination of tissue and stromal antigenic species characteristic of a tumor tissue and associated connective tissue that has been processed with glutaraldyhude and is capable of demonstrating the tumor inhibiting activity of the glutaraldyhe processed tissue preparations described herein.

The term "PTE vaccine" refers to a tissue preparation that possesses a combination of tissue and stromal antigenic species characteristic of a tumor tissue and connective tissue that has been processed with potassium thiocyanate and is capable of demonstrating the tumor cell inhibiting activity of the potassium thiocyanate processed preparations and extracts described herein.

The term "xenogeneic" refers to a tissue or other material that is obtained form a source that is distinct from another, such as not having been obtained from the same species of animal (human vs. rat), or same type of animal tissue (heart vs. lung).

DESCRIPTION

The presently described compositions and tissue preparations provide anti-cancer and anti-tumor vaccines that prevent and/or inhibit cancer and tumor growth in vivo.

The tissue preparations may be described as processed tissue preparations in which a heterologous mixture of tumor antigenic species characteristic of intact tumor tissue and surrounding connective and stromal tissue has been preserved. In some embodiments, the processed tissue preparation comprises a whole tumor tissue and connective (stromal) tissue sample that has been treated with glutaraldehyde- (GFT) or potassium thiocyanate (PTE).

Various embodiments of the tissue preparations comprise cells and tissues harvested directly from and/or surrounding a tumor as it exists in vivo. These tissue preparations have been found to prevent the development of and growth of cancer and tumors. The tissue preparations and vaccines comprise a mixed population of neoplastic cells and supporting connective tissues. The tissue preparations are thus composed of many antigenically different proteins. Furthermore, embodiments of the present invention do not use specific cancer cells, but rather tumor tissue (harvested after in vivo growth) comprised of multiple cell types (neoplastic cells, connective tissue, etc.). In addition, the tissue preparations and vaccines comprise tumor and connective (stoma!) tissue antigenic species that are expressed in vivo.

Other embodiments of the invention will be apparent to those of skill in the art from consideration for the specification and practice of the invention disclosed herein. It is intended that the specification and examples be considered as exemplary only. The true scope and spirit of the invention may better be appreciated as set forth in the claims.

Example 1

Materials and Methods

The present example sets forth the materials and methods employed in some of the embodiments of the invention, and as used throughout the description of the present invention.
Vaccine Preparations.

Two vaccine preparations were evaluated. Vaccine GFT was a glutaraldehyde-fixed tumor (GFT) suspension of cells harvested from tumors grown in animals. Vaccine PTE was a potassium thiocyanate extract (PTE) of harvested tumor tissue. Both Vaccine GFT and vaccine PTE were prepared from tumor tissue. Specifically, three grams of a subcutaneous tumor tissue was harvested from a Lobund-Wistar rat and used in the vaccine preparation. The subcutaneous tumor had been produced by administering prostate adenocarcinoma cells isolated from an autochthonous, metastatic prostate adenocarcinoma in a LW rat (See Pollard M, Luckert P H (1975)10).

The tissue was finely minced, repeatedly aspirated with a 1 cc syringe, and an aliquot drawn with a 20-gauge needle to eliminate large aggregates to create a cell suspension in modified Eagle's medium (MEM). A portion of the cell suspension was incubated in 2.5% glutaraldehyde (v/v) at 37° C. for 120 minutes and then washed thoroughly with media to produce the GFT cell preparation. Another portion was incubated in 1M KSCN and processed following previously described methods to produce a lysate, PTE (See Suckow M A, et al. (1991)[11]; and Ringler D H, et al. (1985)[12]). The PTE was then concentrated to 1.0 mg/ml for use in vaccination.
Animals.

LW rats obtained from a breeding colony maintained at the University of Notre Dame were used for all studies. In this model, large autochthonous prostate tumors develop in approximately 30% of males following a single dose of methylnitrosourea (See Pollard M, Luckert P H. (1986)[13]; and Pollard M., Luckert, P H. (1987)14).
Testosterone Assay.

Sera were assayed for testosterone using a commercial RIA kit (DSL-4000; Diagnostic Systems Laboratories, Inc.; Webster, Tex.). The test protocol recommended by the company was followed. The assays were performed directly with untreated serum, and with a sensitivity of 0.18 ng of testosterone/ml serum.
Study Design.

Rats were vaccinated subcutaneously with a 50:50 mixture of the vaccine preparation with Freund's complete adjuvant for the first dose and incomplete Freund's adjuvant for all subsequent doses. Each dose consisted of $5 \times 10^6$ GFT cells (GFT Vaccine), 0.5 mg of PTE protein (PTE Vaccine); or media (Control). The doses were chosen empirically based upon experience with bacterial vaccines.
Statistical Analysis.

Results of tumor occurrence were compared between groups using the Chi-square test with two degrees of freedom. Differences were considered significant when $p<0.05$. Results for serum testosterone analysis were compared with the Wilcoxon rank sum test with significance reached when $p<0.05$.

Example 2

Vaccination with Tumor Vaccine Prevents De Novo Tumors

The present example is presented to demonstrate the utility of the invention for the prevention of de novo human prostate cancer growth.

The present invention demonstrates that vaccination of LW rats with a GFT whole cell preparation reduced the incidence of autochthonous prostate cancer by 90%, and vaccination with a PTE preparation reduced the incidence by 50%. These results reflect the complex heterogeneity of tumors beyond individual tumor cell types or antigens. The vaccine preparations of the present invention included antigens contributed not only by neoplastic cells, but also by the extensive connective tissue matrix within and surrounding a tumor. These antigens represent powerful immunogens, the sum of which elicits a protective response to the development of prostate cancer. That serum testosterone or testicle weights were not different in vaccinated rats versus controls indicates that the protective response was not due to anti-androgen activity. Further, the normal histological appearance of prostate-seminal vesicle tissue from rats lacking grossly visible tumors suggests that the protective immune response was not directed against antigens predominant in normal tissue.

The above-described results demonstrate that autochthonous prostate cancer may be prevented by vaccination. Further, the results demonstrate that the spleen plays an important role in this response, suggesting that the protective mechanism may involve cell-mediated immunity.

In the present example, a Lobund-Wistar rat MNU-induction model was used to demonstrate that vaccination with preparations derived directly from tumor tissue stimulates protective immunity against development of autochthonous prostate cancer. This model replicates many aspects of the human disease, including development of androgen-independent, autochthonous tumors which are refractory to therapy (Pollard M. (1998)15).

For the long-term study to evaluate the ability of vaccination to prevent development of autochthonous prostate cancer, groups of 30 rats were vaccinated monthly beginning at three months of age and continuing through 12 months. The animals were vaccinated with a GFT vaccine, PTE vaccine, or media (control) vaccine.

At four months of age, rats were administered an intravenous dose (30 mg/kg) of MNU, a cancer causative agent (Ash Stevens, Detroit, Mich.). At 12 months of age, rats were euthanized, serum harvested and frozen at −20° C. for testosterone assay, and necropsied. The weights of testicles were noted, and prostate-seminal vesicle complexes were fixed in 10% neutral buffered formalin for later staining with H & E (haematoxylin and eosin) in preparation for histological evaluation Results from the long-term study are shown in FIG. 1. Of the control animals, about 34% (10/30) rats vaccinated with media, developed grossly visible autochthonous prostate tumors. In contrast, only about 16% (5/30) of the PTE-Vaccine treated rats, and only about 3% (1/30) GFT Vaccine treated rats developed tumors, significantly fewer than the media-vaccinated controls. Rats that did not have grossly visible tumors in the prostate-seminal vesicle complex did not have histological evidence of neoplasia.

Figure 2:
FIG. 2, in accordance with one embodiment of the invention, provides an image showing normal prostatic acini from a rat dosed once with methylnitrosourea and vaccinated monthly with GFT cells for 9 months. The section was stained with H & E and magnified 100×.

Further, prostate-seminal vesicle complexes from rats lacking grossly visible tumors showed normal histological features. No evidence of inflammation or atrophy was noted in prostates from any rats vaccinated with GFT or PTE vaccine, suggesting that the protective immunity was not directed against antigens predominant in normal tissue (FIG. 2).

Figure 3:
FIG. 3, in accordance with one embodiment of the invention, provides an image showing a section of an autochthonous prostate mass from a rat dosed once with methylnitrosourea and vaccinated monthly with media for 9 months. The section was stained with H & E and magnified 100×.

Tumors were adenocarcinomas, typical of those previously described in this model (FIG. 3) (See Pollard M (1998)[15]). There were no significant differences in serum testosterone concentrations at any individual time point or in the weights of testicles between any of the vaccination groups.

The inflammatory responses in tumors from GFT-vaccine treated rats and PTE-vaccine treated rats were distinguished by an influx of eosinophils compared to the responses in tumors from media-vaccinated rats.

The inflammatory response at the tumor margin was evaluated by enumerating mononuclear and granulocytic inflammatory cells over ten high-powered (40× objective) fields. The results are expressed as percentages of total inflammatory cells by. cell type. Necrotic foci within tumors from all three groups were located distant to tumor margins and blood vessels, and included an influx of neutrophils. At the tumor margins, where the immune system might be expected to mount an active response to the expanding tumor, the inflammatory response in a Control vaccine treated animal was composed primarily of neutrophils (74%), lymphocytes (12%), and macrophages (14%). In contrast, the inflammatory response at the margin of a tumor from a GFT vaccine treated animal was composed of eosinophils (33%), neutrophils (27%), lymphocytes (22%) and macrophages (18%). In PTE-vaccinated rats, the inflammatory response at the tumor margin was composed of eosinophils (22%), neutrophils (29%), lymphocytes (28%), and macrophages (21%).

The marked tumor-associated tissue eosinophilia at the tumor margins of GFT-vaccinated and PTE-vaccinated rats distinguishes those inflammatory responses from that observed in tumors from media-vaccinated rats. Tumor-associated eosinophilic infiltrate has been shown to be a favorable prognostic indicator in colorectal carcinoma and early esophageal squamous cell carcinoma (See Fernandez-Acerno MJ, et al. (2000)[30]; and Ohashi Y, et at. (2000)[31]). Activated eosinophils or their culture supernatants significantly inhibited the growth of the cultured human prostate cancer cells (Furbert-Harris P, et aL (2003)[32]). Large numbers of eosinophils were present at tumor margins in GFT Vaccine- and PTE-Vaccine treated rats. Both of these treated groups developed significantly fewer tumors than Control (media) Vaccine treated rats. A possible role for eosinophils in the protective immune response conferred by GFT cell and PTE vaccination may exist.

Example 3

Tissue Vaccine for Treatment of Tumors

The present example demonstrates the utility of the invention to elicit protective immune response following a short term immunization regimen employing the tissue-vaccine preparations of the present invention.

To evaluate the role of the spleen in generating the protective immune response following vaccination, three (3) groups of ten (10) rats were vaccinated initially with one of three (3) vaccine treatments, GFT Vaccine, PTE Vaccine or Control (media) Vaccine, and boosted seven days later. Fourteen days after initial vaccination, rats were euthanized, spleens aseptically harvested and dissociated into MEM using a screen, and co-incubated for three hours at 37° C. with harvested tumor cells (1:1 ratio of splenocytes:tumor cells). The cell suspension was then administered subcutaneously into the flank of naive LW rats such that each rat received a volume containing $2 \times 10^6$ cells. Rats were euthanized 28 days later and the presence or absence of grossly observable tumors noted.

Figure 4:
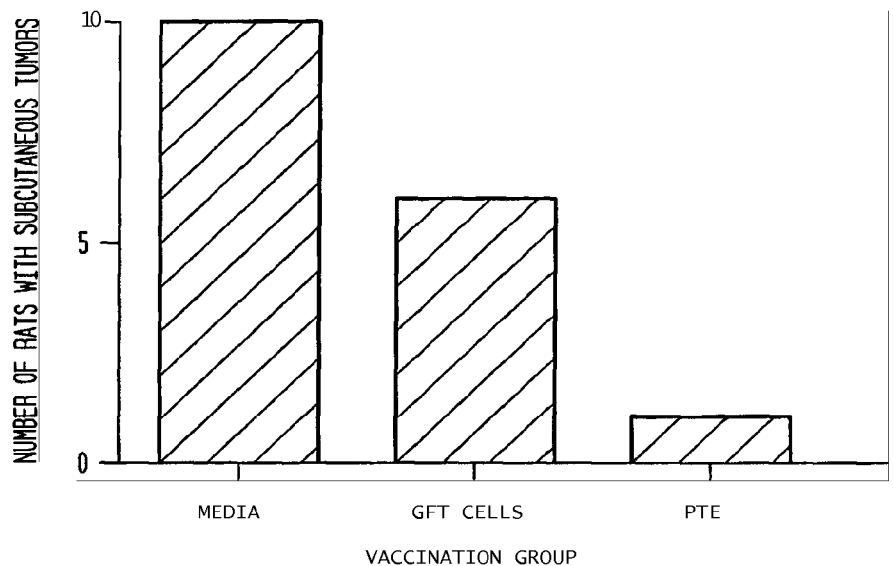
FIG. 4, in accordance with one embodiment of the invention, provides a graph showing the number of rats with subcutaneous tumors following administration of tumor cells which had been incubated with splenocytes from either media-vaccinated, GFT cell-vaccinated or PTE-vaccinated rats.

Results from the short-term vaccination study are shown in FIG. 4. All 10/10 (100%) of the rats administered a vaccine prepared from tumor cells co-incubated with splenocytes from Control (media)-vaccinated rats developed subcutaneous tumors. In contrast, only 60% (6/10) and 20% (2/10) of the animals administered a vaccine prepared from tumor cells co-incubated with splenocytes from GFT-vaccinated and PTE cell-vaccinated rats, respectively, developed tumors. Both of these groups had significantly fewer rats with tumors compared to rats receiving tumor cells which had been co-incubated with splenocytes from control (media)-vaccinated rats.

Example 4

Repeated Vaccination with Tumor Tissue Vaccine does not Result in Autoimmune Disease The present example demonstrates that vaccination with the tumor tissue vaccines of the present invention does not result in the development of autoimmune disease.

Animals were subjected to repeated vaccinations of the tumor tissue vaccines and then examined for the existence of any histological evidence of autoimmune disease. Groups of 10 three-month-old LW rats were each immunized and boosted monthly for 12 months with MEM (control), PTE vaccine or GFT vaccine. Freund's complete adjuvant was used in the initial vaccination, and Freund's incomplete adjuvant was used in the booster vaccinations. Tissues were then harvested from the animals at 15 months of age, fixed in 10% neutral buffered formalin, sectioned at 3-4 i.tm and stained with hematoxylin and eosin. All rats were clinically normal for the duration of the study. Kidney, heart, brain, liver, testis, prostate/seminal vesicle, and spleen were examined and all found to be histologically normal.

The results demonstrate that repeated immunization with a tumor tissue vaccine, such as the PTE or GFT tumor tissue vaccine preparations, does not induce tissue damage related to autoimmunity.

Example 5

The Protective Effect of Tumor Tissue Vaccination does not' Result from Serum Antibody To determine if serum factors, such as antibody, are responsible for the protective effect associated with vaccination, two rats each vaccinated subcutaneous with MEM with adjuvant (Control vaccine); PTE processed tumor cells with adjuvant; or GFT processed tumor cells with adjuvant. Rats were boosted once, 7 days after initial vaccination. Freund's complete adjuvant was used in the initial vaccination, and Freund's incomplete adjuvant was used in the booster vaccination. Seven days after the booster vaccination, the rats were euthanized and serum harvested.

Tumor cells harvested from a subcutaneously passaged tumor were then incubated at a dilution of $8\times10^6$ cells per ml of harvested serum for 3 hours at 37° C. A volume of about 0.25 ml of this suspension (equivalent to about $2\times10^6$ cells) was administered subcutaneously in the flank of LW rats (6/group). Rats were then necropsied 3 weeks later and the number of animals bearing tumors was compared. The results (number having tumors/total number per group) were:

PTE rats=5/6

GFT cell rats=6/6

MEM rats=6/6

This study suggests that humoral antibody is not responsible for the protective immune response demonstrated in tumor tissue vaccine treated animals.

Example 6

Vaccination with Tumor Tissue Vaccines Reduces the Size of Transplanted Tumors and Inhibits Metastasis from the Primary Tumor To determine if vaccination has a protective effect against metastasis from a primary tumor, groups of ten rats were vaccinated subcutaneously with media, GFT vaccine, or PTE vaccine and boosted weekly for two weeks. Freuend's complete adjuvant was used in the initial vaccination, and Fruend's incomplete adjuvant was used in booster vaccinations. At the time of the second boost, $2\times10^6$ cells harvested from a subcutaneously passaged LW prostate tumor were administered to each rat, subcutaneously. Six weeks later, the rats were euthanized. Weights of subcutaneous tumors were:

Media control=11.44 gm

PTE=9.15 gm

GFT cells=8.88 gm

Group differences were not significant (P>0.05) but there appears to be a trend toward reduced tumor size in vaccinated groups.

Figure 5:
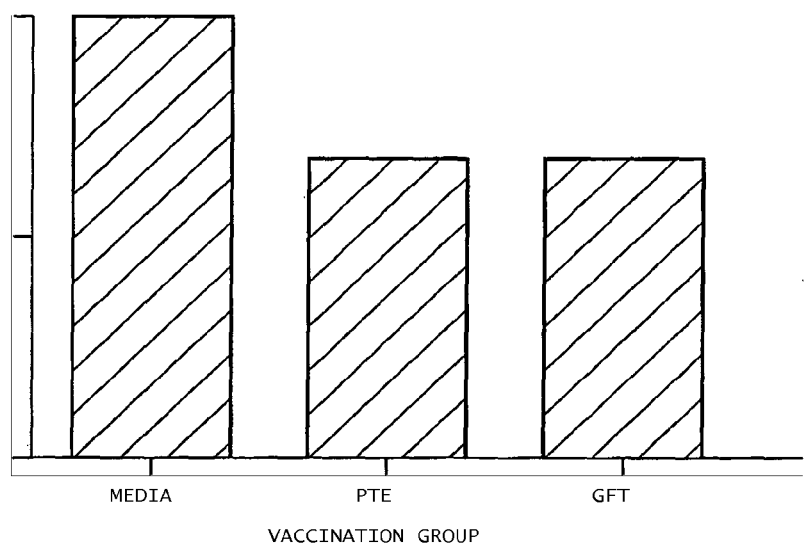
FIG. 5, in accordance with one embodiment of the invention, provides a graph showing the percentage of vaccinated rats with primary tumors having metastatic foci to the lungs.

For lung metastases, 100% (10/10) of the Control (Media) rats had metastatic foci in the lungs; 70% (7/10) of the PTE-tumor cell vaccinated rats had metastatic foci in the lungs; and 70% (7/10) of the GFT tumor cell-vaccinated rats had metastatic foci in the lungs. These results, depicted in FIG. 5, demonstrate that a protective effect was provided' in the tumor cell vaccinated animals.

The results of this study demonstrate that vaccination with a vaccine that includes—tumor cells effectively reduces the size of existing tumors and inhibits metastasis from the primary tumor.

Example 7

Vaccination with the Tumor Tissue Vaccine Reduces Growth of Metastatic Tumor Foci Following Resection of a Primary Tumor To evaluate the effect of vaccination on metastasis following resection (Res) of a primary tumor, subcutaneous tumors were produced in 3-month-old LW rats by administering $2\times10^6$ cells from a subcutaneously passaged prostate tumor harvested from a LW rat. The resulting subcutaneous tumors were surgically resected after 17 days in 33 rats. At the time of resection, 10 rats were immunized with GFT vaccine and adjuvant; 10 rats were immunized with MEM (control) plus adjuvant; 10 rats underwent resection but had no further treatment; and 3 rats did not undergo resection or vaccination. All vaccinated rats underwent booster vaccination weekly for 3 weeks. Initial vaccination included Freund's complete adjuvant, and booster vaccinations included Freund's incomplete adjuvant. Six weeks after resection, rats were euthanized and necropsied; the metastatic foci on the pleural surfaces of the lungs were counted and measured with a caliper.

Mean numbers of lung foci:

Resection only=20.40 gm (SD 5.2)

Res.+GFT=11.60 gm (SD 7.9) Res.+media=22.67 gm (SD 7.2) No resection=17.00 gm (SD 1.0)

There was no significant difference in the mean number of lung foci observed in rats which underwent resection followed by vaccination with GFT vaccine compared to animals which underwent resection only (P<0.05); and between rats which underwent resection followed by vaccination with GFT vaccine compared to animals which underwent resection followed by vaccination with control vaccine (media) (P<0.01).

Figure 6:
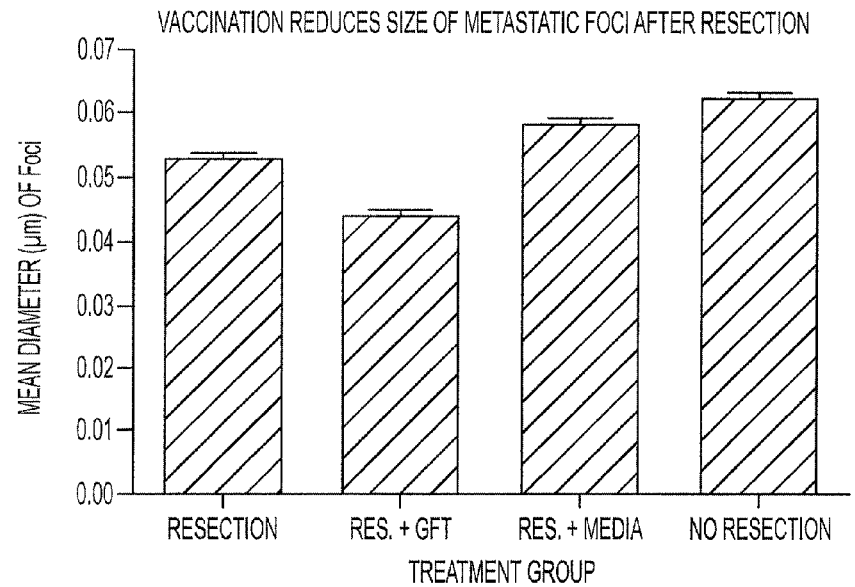
FIG. 6, in accordance with one embodiment of the invention, provides a graph showing the size of metastatic foci in the lungs following resection of the primary tumor and vaccination.

The mean diameter (lam) for lung foci are depicted in FIG. 6 and were:

Resection only=0.053 (SD 0.017)

Res.+GFT=0.046 (SD 0.018)

Res.+Media=0.058 (SD 0.020)

No resection=0.062 (0.023)

There is a significant difference in the mean diameter of metastatic foci observed in the lungs between rats undergoing resection only and rats undergoing resection followed by vaccination with GFT vaccine (P<0.05); between rats undergoing resection followed by vaccination with GFT vaccine and rats undergoing resection followed by vaccination with a control (media) vaccine (P<0.001); and between rats undergoing resection followed by vaccination with GFT vaccine and rats not undergoing resection (0.001). The significant reduction in size of metastatic foci in rats undergoing resection and GFT vaccination compared to all other groups indicates that growth of metastases are suppressed by GFT vaccination.

These results show that, while vaccination with GFT vaccine does not reduce the number of metastatic foci compared to resection alone, vaccination reduces the growth of metastatic foci.

Example 8

Xenogeneic Vaccination with Non-Human Tumor Tissue Vaccine Stimulates Protective Immunity Against Human Cancer Cells Immunization with xenogeneic DNA is an attractive approach in the treatment of cancer because it generates T cell and antibody responses (Srinivasan and Wolchok (2004)[27]). In the present example, a xenogeneic tissue immunization model is set forth that demonstrates the utility of the present invention for providing xenogeneic tumor vaccines that protect against human cancer cell growth. In the present example, rat tumor tissue was used to prepare a tumor tissue vaccine. The data presented here demonstrates the efficacy of the tumor tissue vaccines for the prevention and treatment of cancer, particularly for prostate cancer.

Testosterone pellets (12.5 mg) were implanted subcutaneously into each of 30 athymic nude mice (NCR Balb/C). The testosterone was administered to prepare the in vivo environment for growth of transplanted human prostate cancer cells as described below.

Groups of five immunocompetent male (NCr)-Foxnl <nu> (Tac) mice (8 weeks old) were immunized subcutaneously with either MEM (Control), a GFT vaccine (1×106 GFT tumor cells), or left non-immunized. This is the background strain for the athymic nude mice described herein. The mice in each of these treatment groups were boosted weekly for 3 weeks. Freund's complete adjuvant was used in the initial vaccination, and Freund's incomplete adjuvant was used in booster vaccinations. One week after the final booster vaccination, mice were euthanized and their spleens and serum harvested. Spleens were aseptically harvested, dissociated, pooled for each group, and the red blood cells lysed with ammonium chloride solution. The remaining splenocytes were incubated in modified Eagles medium (MEM) for 3 hours at 37° C. with PC346 human prostate cancer cells (1:4 ratio of mouse splenocyte:PC346 human prostate cancer cells).

Nude mice were anesthetized and prepared for aseptic surgery. Ten mice per each vaccination group were implanted (via orthotopic administration into the prostate gland) with 40,000 PC346 human cancer cells+10,000 mouse splenocytes in Matrigel® (BD Biosciences®, Parsipanny, N.J.). Several animals died prior to scheduled harvest, with gross necropsy being non-diagnostic due to advanced autolysis. Eight weeks later, all remaining animals were euthanized and evaluated for the presence of prostate tumors. Prostate/seminal vesicle (PSV) weights were obtained, and tissue fixed in formalin. Fixed tissue was later sectioned at 3-4 um and stained with hematoxylin and eosin.

Figure 7:
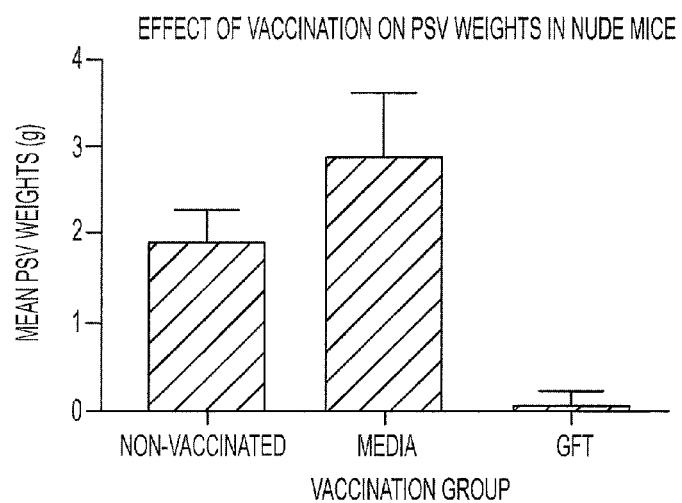
FIG. 7, in accordance with one embodiment of the invention, provides a graph showing the weights of prostate-seminal vesicle (PSV) complexes in nude mice transplanted with human PC346 prostate cancer cells which had been co-incubated with splenocytes from immunocompetent mice which were not vaccinated or which had been vaccinated with either media or GFT vaccine (of rat tissue origin FIG. 8, in accordance with one embodiment of the invention, provides a graph showing the percentage of nude mice with histological evidence of growth of transplanted human PC346 prostate cancer cells. These mice were transplanted orthotopically with PC346 cells which had been co-incubated with splenocytes from immunocompetent mice which were either not vaccinated or which had been vaccinated with either media or GFT vaccine (of rat tissue origin).

Results for prostate/seminal vesicle (PSV) weights (FIG. 7) are:

Non-Vaccinated=1.90 gm (SD 1.11)

MEM (Control) Vaccinated=2.87 gm (SD 2.00)

GFT Tumor Vaccinated=0.38 (SD 0.499)

There was a significant difference observed between GFT Tumor Vaccinated and Media (Control) Vaccinated (P<0.01) PSV weights; and between GFT Tumor Vaccinated and Non-vaccinated (P<0.05) PSV weights.

Figure 8:
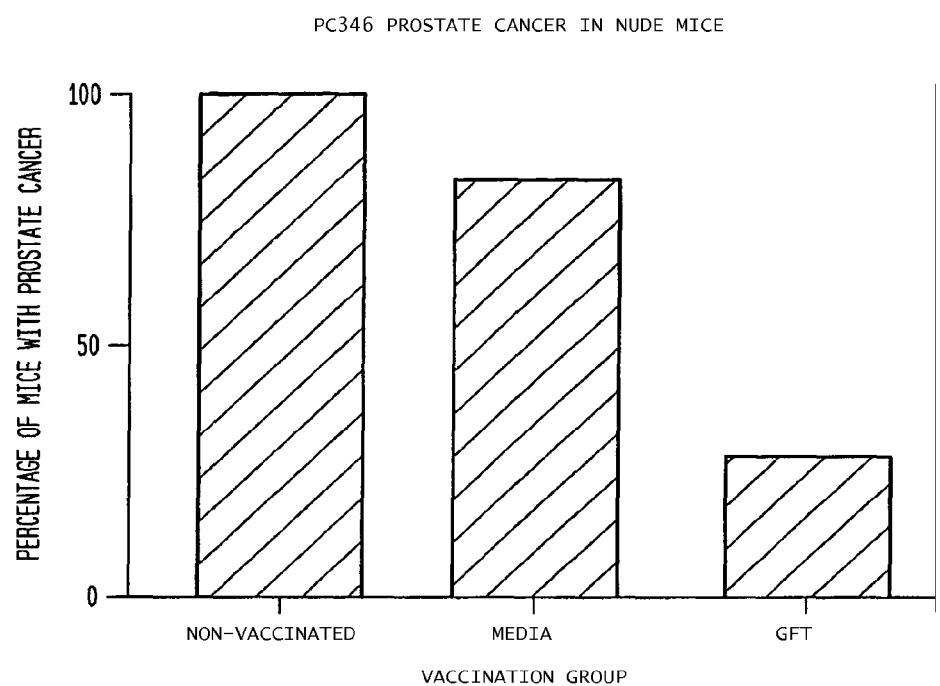

Histologic examination showed that PSV complexes weighing less than 0.84 gm did not demonstrate any evidence of tumor growth. Based on this, the incidence of animals with prostate tumors (FIG. 8) is:

Non-Vaccinated=100% (7/7 animals)

MEM (Control) Vaccinated=83.3% (5/6 animals)

GFT Tumor Vaccinated=28.6% (2/7 animals)

Significantly fewer mice (p<0.01, Chi-square analysis with 2 degrees of freedom) administered human PC346 cells previously co-incubated with splenocytes from mice vaccinated with the GFT vaccine, had tumors at the time of necropsy, compared to mice administered human PC346 cells previously co-incubated with splenocytes from MEM (Control) vaccinated mice, or compared to the number of mice administered PC346 cells co-incubated with splenocytes from mice that had not been vaccinated at all (Non-Vaccinated). This shows that xenogeneic vaccination with the GFT vaccine stopped the development and progression of prostate cancer.

Activity against the human PC346 cells demonstrates efficacy of the vaccine against existing neoplastic cells, such as those in mature tumors, and also protection in a xenogeneic species (mouse) and against a xenogeneic cell line (human PC346 cells). This demonstrates evidence of homologous antigens between rat cancer cells and human cancer cells, and particularly homologous antigens between rat prostate tumor cells and human prostate cancer cells.

The GFT tissue vaccine and the PTE tissue vaccine prevent prostate cancer. Further, the vaccines can be used to target existing cancers. Vaccination with these preparations reduces the growth of primary transplanted tumors and of metastatic tumor foci. Following resection of the primary tumor, this trend persists with a significant reduction in the size of metastatic tumor foci. The tissue vaccines also have a striking efficacy as a xenogeneic cancer vaccine.

It is believed that xenogeneic vaccines allow the immune system to overcome tolerance to self-antigens expressed by tumors, thus stimulating a vigorous immunity to homologous antigens. In this way, xenogeneic vaccines have advantage over autologous or even allogeneic vaccines. The vaccine preparations are mixtures which contain a variety of potent antigens. In the case of prevention, the immune systems of vaccinated animals rapidly respond to preneoplastic lesions and effectively target occasional cancer cells as they develop. In the case of treatment, the immune system faces the much greater challenge of targeting an enormous number of active cells which can induce immune tolerance and quickly alter phenotype to adapt to selective pressures from treatment. The vaccines also include connective tissue components which are not neoplastic but which may be altered by cytokine or other signals from the neoplastic cells to organize needed connective tissue and stromal infrastructure for tumor support, growth, and progression. Because these connective tissue components are not neoplastic, they cannot alter their immunophenotype as easily as neoplastic cells in order to evade an immune response resulting from vaccination with a vaccine directed against these components. In this way, then, vaccination against tumor connective tissue and stromal components allows a protective immune response that the tumor cannot escape by rapidly altering immunophenotype, an escape mechanism commonly employed by neoplastic cells.

Example 9

Hormone Responsive Tissue Associated Tumor and Cancers

The examples presented herein demonstrate that vaccines derived directly from animal tumor tissue can be used to prevent and treat prostate cancer. This approach can be generalized to other tumors, including breast, lung, testicular, uterine, and ovarian cancers. All of these cancers depend upon an extracellular connective tissue stroma to provide tumor infrastructure. One of the features of the tissue vaccines disclosed herein is that they include components derived from stroma and tumor tissue. The immunity provided by the present vaccine preparations to antigenic epitopes within the stroma is believed to contribute to the overall efficacy of the vaccine.

Many cancers, such as prostate cancer, cancers of the breast, uterus, ovary, and testicle, arise from a hormonally active tissue. All of these cancers are believed to be influenced to at least some degree by the hormonal status of the individual. This relationship suggests that similar mechanisms may be involved for these cancers with respect to tumor initiation and progression. The presently described tumor tissue vaccines against prostate cancer therefore have import in the development of vaccines for other cancers characteristic of other hormonally active tissues.

Prostate and breast cancer, and most forms of lung cancer, manifest as adenocarcinomas. These cancers thus arise from epithelium of glandular structures. Commonly, they are aggressive and metastatic. Aggressive forms of these cancers quickly become refractory to treatment. The similar origins and behaviors of these cancers suggest that they may have common mechanisms by which they arise and progress. For this reason, the presently described methods for vaccination to prevent and treat prostate cancer are also particularly relevant to the prevention and treatment of both lung and breast cancer.

Example 10

GFT Tissue vs. PTE Tissue Vaccine

The present example is presented to demonstrate the utility of the present invention for providing anti-tumor vaccine preparations.

Two vaccines were evaluated. One of these vaccines was an extract (PTE) of cells harvested directly from in vivo tumors. The other vaccine was a preparation of glutaraldyhyde-processed tumor and connective tissue (GFT) cells.

In a model where splenocytes from vaccinated rats were incubated with rat live tumor cells prior to transplantation into homologous rats, PTE tissue vaccination resulted in an 80% reduction of subcutaneous tumors versus a 40% reduction resulting from GFT cell vaccination. In a long-term model where de novo prostate tumor formation was studied following vaccination, GFT tissue vaccination resulted in a 90% reduction in tumor formation versus a 50% reduction following PTE tissue vaccination.

The GFT-tissue vaccine logically contains a significant amount of antigens that would be expressed on the tumor cell surface. In contrast, the PTE-tissue vaccine contains antigens typically present in the tumor cytosol. While not intending to be limited to any particular theory or mechanism of action, the differences in antigen origin and composition between these two tissue vaccines may at least in part explain the differences observed in their activity against de novo tumor formation and subcutaneous tumor formation from transplanted mature tumor cells.

In the case of transplanted tumors, the immune response is directed against mature tumor cells which are being directly transplanted into the animal. These transplanted cells contained a mix of neoplastic cells, stroma, and connective tissue. As mature tumor cells, they actively release cytokines to further promote tumor progression and growth. The site of cytokine production is the cytosol. Thus, the PTE vaccine may contain a mixture of antigens which is more relevant to and efficient at protection against growth of mature tumor cells compared to the GFT cell vaccine as demonstrated in the transplantation model. However, both preparations provided significant anti-tumor activity.

The de novo model of autochthonous prostate tumor formation involves transformation of normal prostate epithelium into neoplastic tissue which eventually forms a tumor. As individual neoplastic cells arise, the most dominant antigens are—cell surface antigens, since the cytosolic machinery of a small number of neoplastic cells is not able to produce and elaborate significant amounts of the cytokines needed for tumor maturation and progression. Because the immune response associated with the GFT tissue vaccine is associated primarily with cell surface antigens, the immune system is more efficient at halting these de novo preneoplastic lesions than the PTE tissue vaccine.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

BIBLIOGRAPHY

The following references are hereby specifically incorporated herein by reference.
1. Boring C C, et al. (1993), Cancer statistics. *CA Cancer J Clin,* 43:7-26.
2. Nomura Amy et al. (2000), *Cancer Epid Biomark Pre$^y$,* 9:883-87.
3. Brooks J D, et al. (2001), *J Urol* 2001; 166:2034-8.
4. Hursting S D, et al. (1990), *Pre$^y$ Med,* 19:242-53.
5. Gann P H. (1999), *JAMA,;* 281:1682.
6. Gann P H, Ma J, Giovannucci E, et al. (1999), *Cancer Res.,* 59: 1225-30.
7. Tjoa B A, et al. (1999), *Prostate;* 40:125-29.
8. Tjoa B A, Murphy G P. (2000), *Immunol Lett,* 74:87-93.
9. Gulley J, et al. (2002), *Prostate,* 53:109-17.
10. Pollard M, Luckert P H. (1975), *J Natl Cancer Inst,* 54:643-49.
11. Suckow M A, et al. (1991), *Lab Anim Sci.,* 41:151-56.
12. Ringler D H, Peter G K, Chrisp C E, et al. (1985), *Infect. Immun.,* 49:498-504.
13. Pollard M, Luckert P H. (1986), *J Natl Cancer Inst,* 77:583-87.
14. Pollard M, Luckert P H. (1987), *Prostate,* 11:219-27.
15. Pollard M. (1998), *Prostate,* 37:1-4.
16. Hrouda D, et al. (1998), *Br J Urol.,* 82:870-76.
17. Hrouda D, et al. (2000), *Br J Urol Int,* 86:742-48.
18. Griffith T S, et al. (2001), *J Natl Cancer Inst,* 93:998-1007.
19. Charles L G, et al. (2000), *World J Urol,* 18:136-42.
20. Michael A, et al. (2005), *Clin Cancer Res,* 11:4469-78.
21. U.S. Pat. No. 6,406,689—Falkenberg et al.;
22. Wang et. al (1993), J. Clin. Invest., 91:684-692;
23. Shekhar et al (2001), Cancer Res., 61:1320-1326.
24. Cunha etal (2003), *Int. J. Cancer,* 107:1-10.
25. Yu-quan Wei (2002), *Anti-Cancer Drugs,* 13:229-235.
26. Fong et al. (2001), *J. Imm.,* 167: 7150-7156.
27. Srinivason et al. (2004), *l Translational Med.,* 2:1-12.
28. Bergman et al. (2003), *Clin. Canc. Res.,* 9: 1284-1290.
29. Qui-ming He et al. (2003), *J. Biol. Chem.,* 278 (24): 21831-21886.
30. Fernandez-Acerno MJ, et aL (2000), *Cancer* 88: 1544-48.
31. Ohashi Y, et al. (2000), *Anticancer Res.,* 20: 3025-30.
32. Furbert-Harris et al. (2003), *Prostate,* 57:165-175.

What is claimed is:
1. A method of treatment comprising inhibiting prostate tumor growth, said method comprising:

a first treatment with an effective amount of a non-viable whole prostate tumor tissue preparation and stromal tissue; and a subsequent treatment with an effective amount of the preparation, wherein prostate tumor growth is inhibited.

2. The method of claim 1, wherein the preparation of the first treatment comprises about $5\times10^6$ cells of a GFT treated whole prostate tumor tissue preparation.

3. The method of claim 1, wherein the preparation comprises an effective dose of the whole prostate tumor tissue preparation and an adjuvant.

4. The method of claim 1, wherein the subsequent treatment is administered about 7 days after the first treatment.

5. The method of claim 1 wherein the prostate tumor growth inhibited is human prostate tumor growth.

6. The method of claim 1 wherein the preparation of the first treatment comprises a 50:50 mixture of the preparation and an adjuvant.

7. A method of treatment comprising inhibiting prostate tumor growth, said method comprising:

administering an effective amount of a non-viable whole prostate tumor tissue preparation and connective tissue to an animal; and inhibiting de novo prostate tumor growth.

8. The method of claim 7, wherein the animal is a human.

9. The method of claim 7, wherein the prostate tumor tissue comprises human prostate tumor tissue.

10. The method of claim 7, wherein the whole prostate tumor tissue preparation is a glutaraldehyde processed tumor tissue preparation.

11. The method of claim 7 wherein the prostate tumor growth inhibited is human prostate tumor growth.

12. The method of claim 7 when the whole tumor tissue preparation comprises a 50:50 mixture of the preparation and an adjuvant.

* * * * *